United States Patent

Morita

Patent Number: 5,972,681
Date of Patent: Oct. 26, 1999

[54] CALCIUM-REQUIRING PROTHROMBIN ACTIVATOR

[75] Inventor: Takashi Morita, Saitama, Japan

[73] Assignee: Eisai Co., Ltd., Tokyo, Japan

[21] Appl. No.: 08/894,403

[22] PCT Filed: Feb. 29, 1996

[86] PCT No.: PCT/JP96/00479

§ 371 Date: Aug. 18, 1997

§ 102(e) Date: Aug. 18, 1997

[87] PCT Pub. No.: WO96/27660

PCT Pub. Date: Sep. 12, 1996

[30] Foreign Application Priority Data

Mar. 3, 1995 [JP] Japan ................................. 7-044340
Feb. 22, 1996 [JP] Japan ................................. 8-035207

[51] Int. Cl.[6] .............................. C12N 9/48; C12N 9/50; A23J 1/00
[52] U.S. Cl. .......................... 435/219; 435/212; 530/412; 530/413; 530/856
[58] Field of Search .................................. 435/212, 219; 530/412, 413, 856

[56] References Cited

U.S. PATENT DOCUMENTS 5,453,370 9/1995 Triplett et al. .......................... 435/214

OTHER PUBLICATIONS

Poller, L., "Progress in Standardisation in Anticoagulant Control," Hematology Review, vol. 1 (1987) pp. 225–241.

Latallo, et al., An Evaluation of Chromogenic Substrates in the Control of Oral Anticoagulant Therapy, British Journal of Haematology, vol. 47 (1981) pp. 307–318.

Poller, et al., "Dosage and control of oral anticoagulants," British Journal of Haematology, vol. 51 (1982) pp. 479–485.

Rosing, et al., "Structural and Functional Properties of Snake Venom Prothrombin Activators," Taxicom, vol. 30, No. 12 (1992) pp.g 1515–1527.

Morita, et al. "Prothrombin Activator from *Echis carinatus* Venom," Methods in Enzymology, vol. 80 (1981) pp. 303–311.

Speijer, et al., "Platelet Procoagulant Properties Studied with Snake Venom prothrombin Activators," Thrombosis and Haemostasis, vol. 57, No. 3 (1987) pp. 349–355.

Pirkle, et al. "Thrombin–Like Enzymes of Snake Venoms," Thrombosis Research, vol. 8 (1976) pp. 619–627.

Primary Examiner—Karen Cochrane Carlson
Assistant Examiner—Holly Schnizer
Attorney, Agent, or Firm—Birch, Stewart, Kolasch & Birch, LLP

[57] ABSTRACT

An object of the present invention is to provide a novel prothrombin activator. The application of the activator to thrombin-related diseases is expected.

Described is a prothrombin activator derived from snake venom, which is a calcium requiring type and comprises three polypeptide chains composed of one heavy chain having a molecular weight of about 62,000 or about 60,000 and two light chains having molecular weights of about 17,000 and about 14,000, respectively.

11 Claims, 3 Drawing Sheets

SEQUENCE LISTING

```
<160> NUMBER OF SEQ ID NOS: 7

<210> SEQ ID NO 1
<211> LENGTH: 30
<212> TYPE: PRT
<213> ORGANISM: Arabidopsis thaliana
<220> FEATURE:
<223> OTHER INFORMATION: any Xaa = unknown

<400> SEQUENCE: 1

Lys Gln Lys Phe Asp Lys Lys Phe Ile Lys Leu Val Ile Val Val Asp
 1               5                  10                  15

His Ser Met Val Xaa Lys Xaa Asn Asn Asp Leu Ile Ala Ile
            20                  25                  30

<210> SEQ ID NO 2
<211> LENGTH: 30
<212> TYPE: PRT
<213> ORGANISM: Arabidopsis thaliana
<220> FEATURE:
<223> OTHER INFORMATION: any Xaa = unknown

<400> SEQUENCE: 2

Ser Arg Lys Gln Lys Phe Asp Lys Lys Phe Ile Lys Leu Val Ile Val
 1               5                  10                  15

Val Asp His Ser Met Val Xaa Lys Xaa Asn Asn Asp Leu Ile
            20                  25                  30

<210> SEQ ID NO 3
<211> LENGTH: 30
<212> TYPE: PRT
<213> ORGANISM: Arabidopsis thaliana

<400> SEQUENCE: 3
```

```
Asp Cys Leu Pro Gly Trp Ser Ser His Glu Gly His Cys Tyr Lys Val
 1           5               10                  15

Phe Asn Gln Glu Met Tyr Trp Ala Asp Ala Glu Lys Phe Cys
            20              25                  30

<210> SEQ ID NO 4
<211> LENGTH: 30
<212> TYPE: PRT
<213> ORGANISM: Arabidopsis thaliana

<400> SEQUENCE: 4

Asp Cys Leu Pro Asp Trp Phe His Tyr Glu Gly His Cys Tyr Arg Val
 1           5               10                  15

Phe Asp Glu Pro Lys Lys Trp Ala Asp Ala Glu Lys Phe Cys
            20              25                  30

<210> SEQ ID NO 5
<211> LENGTH: 5
<212> TYPE: PRT
<213> ORGANISM: Arabidopsis thaliana

<400> SEQUENCE: 5

Ser Arg Lys Gln Lys
 1           5

<210> SEQ ID NO 6
<211> LENGTH: 5
<212> TYPE: PRT
<213> ORGANISM: Arabidopsis thaliana

<400> SEQUENCE: 6

Asp Cys Leu Pro Asp
 1           5

<210> SEQ ID NO 7
<211> LENGTH: 5
<212> TYPE: PRT
<213> ORGANISM: Arabidopsis thaliana

<400> SEQUENCE: 7

Asp Cys Leu Pro Gly
 1           5
```

CALCIUM-REQUIRING PROTHROMBIN ACTIVATOR

TECHNICAL FIELD

The present invention relates to a novel calcium-requiring prothrombin activator derived from snake venom.

BACKGROUND ART

In the body, the blood circulates under a certain balance between the coagulation system and the fibrinolytic system.

In the second phase of blood clotting, prothrombin (Factor II), which is one of the blood coagulation factors, is converted into thrombin by the action of thromboplastin (Factor III) in the presence of calcium ions ($Ca^{2+}$ ions: Factor IV). In the third phase, fibrinogen (Factor I) is acted upon by the thrombin and changed into strands of fibrin, whereby the blood clotting is completed.

Anticoagulant therapy is given to patients suffering from ischemic heart diseases or patients having a heart valve prosthesis and for the monitoring of the therapy, prothrombin time is measured. The measurement of prothrombin time is carried out by measuring the time required for coagulation by adding thromboplastin, which is an exogenous substance causing blood clotting, to a specimen, whereby the extrinsic coagulation pathway activity can be studied. This method is used for total measurement of extrinsic coagulation factors (Factors I, II, V, VII and X).

Thromboplastin used as a reagent for the above measurement is prepared from an organ-extracted phospholipid so that it differs in the sensitivity according to the products or batches. The measured value therefore does not accurately reflect the amount of coagulation factors in the specimen, which tends to heighten the frequency of hemorrhage caused by excessive administration of an oral anticoagulant and has come to be a serious clinical problem (Poller L. "Progress in standardization in anticoagulant control", Hematol. Rev. 1, 225–241(1987); Latallo Z S, Thomson J M and Poller L, "An evaluation of chromogenic substrates in the control of oral anticoagulant therapy", Br. J. Haematol, 47, 307–318 (1981); Poller L. and Taberner D A, "Dosage and control of oral anticoagulants", An international survey, Br. J. Haematol. 51, 479–485(1982)).

An object of the present invention is to overcome the above-described problem by finding a novel prothrombin activator, applying it to the measurement of prothrombin in the blood and thereby providing a reagent for accurate measurement. An another object of the present invention is to apply the reagent to thrombin-related diseases.

DISCLOSURE OF THE INVENTION

Prothrombin activators which have been separated or identified to date from the snake venom can be classified into three types (Rosing, J. and Tans, G., Toxicon, 30, 1515–1527 (1992)). The enzymes belonging to Group 1 are metalloproteases whose action on prothrombin is independent of any plasma or exogenous cofactors. Those belonging to Group 2 are Gla-containing, factor Xa-like serine proteases that require factor Va, phospholipids and $Ca^{2+}$ ions. Those belonging to Group 3 are hybrid enzymes comprising factor Xa-like catalytic subunits and factor Va-like regulatory subunits and similar to those belonging to Group 2, require phospholipids and $Ca^{2+}$ ions.

It is widely known (T. Morita et al., Methods Enzymol., 80, 303–311, 1981) that metalloproteases which activate prothrombin are present in the venom of Echis carinatus.

The present inventors thought out various devices for assay conditions. Under those conditions, the inventors screened prothrombin activators in the venom of Echis carinatus and succeeded in isolating two calcium-requiring prothrombin activators different from metalloproteases such as ecarin which are known to date. Those two activators were designated as carinactivase-1 and carinactivase-2 (which will hereinafter be abbreviated as "CA-1" and "CA-2"), respectively. As a result of investigation on their activity, it has been found that although ecarin, which is an enzyme known to date, reacts with PIVKA-II (abnormal blood coagulation factor (protein induced by Vitamin K absence or antagonist) of Factor II (prothrombin)) and normal prothrombin, the activators of the present invention do not react with PIVKA-II but only react with normal prothrombin, leading to the completion of the present invention.

The present invention therefore provides a prothrombin activator derived from snake venom, which is a calcium-requiring type protease and more specifically, provides a prothrombin activator which is a metalloprotease. The activator comprises three polypeptide chains composed of one heavy chain having a molecular weight of about 62,000 or about 60,000 and two light chains having molecular weights of about 17,000 and about 14,000, respectively according to the SDS-PAGE analysis.

The activator of the present invention is available by the extraction from the snake venom. By using, for example, the venom of Echis carinatus as the snake venom, a prothrombin activator of the present invention which is a calcium-requiring protease can be obtained.

In addition, CA-1 and CA-2 are almost identical in terms of the molecular size and enzymological features. Concerning the N-terminal amino acid sequence of the heavy chain of CA-1, the heavy chain having a molecular weight of about 62,000 is represented by the sequence described in SEQ ID No: 2, that is, Ser Arg Lys Gln Lys Phe Asp Lys Lys Phe Ile Lys Leu Val Ile Val Val Asp His Ser Met Val Xaa Lys Xaa Asn Asn Asp Leu Ile, while the heavy chain having a molecular weight of about 60,000 is represented by the sequence described in SEQ ID No: 1, that is, Lys Gln Lys Phe Asp Lys Lys Phe Ile Lys Leu Val Ile Val Val Asp His Ser Met Val Xaa Lys Xaa Asn Asn Asp Leu Ile Ala Ile. The N-terminal amino acid sequences of the light chains of CA-1 are represented by the sequence described in SEQ ID No: 3, that is, Asp Cys Leu Pro Gly Trp Ser Ser His Glu Gly His Cys Tyr Lys Val Phe Asn Gln Glu Met Tyr Trp Ala Asp Ala Glu Lys Phe Cys and by the sequence described in SEQ ID No: 4, that is, Asp Cys Leu Pro Asp Trp Phe His Tyr Glu Gly His Cys Tyr Arg Val Phe Asp Glu Pro Lys Lys Trp Ala Asp Ala Glu Lys Phe Cys. In another aspect, CA-1 and CA-2 are almost identical in terms of the molecular size and enzymological features, and the N-terminal amino acid sequences of the heavy chain and the light chains of CA-1 are represented by the Sequence described in the SEQ ID No: 5, that is, Ser Arg Lys Gln Lys, the Sequence described in the SEQ ID No: 6, that is, Asp Cys Leu Pro Asp and the Sequence described in the SEQ ID No: 7, that is, Asp Cys Leu Pro Gly, respectively in the order.

The present invention will hereinafter be described more specifically.

The purification of the activator of the present invention from the snake venom such as the venom of Echis carinatus can be effected by the ordinary purification method for proteins, for example, ion exchange chromatography, affinity chromatography, gel filtration chromatography, adsorption chromatography, reversed phase chromatography or partition chromatography.

The calcium-requiring prothrombin activator of the present invention can be obtained, for example, by purifying the snake venom by gel filtration chromatography on Superdex, affinity chromatography on BLUE SEPHAROSE®, and then chromatography on a strong base resin such as Q Sepharose.

In particular, the calcium-requiring prothrombin activator of the present invention can be separated and purified easily by using BLUE SEPHAROSE® obtained by immobilizing Civachrone blue F3GA on Sepharose.

The activity of prothrombin activation of fractions obtained in respective purification steps and the purified target product can be measured in accordance with the method of Morita and et al. (T. Morita et al., Methods Enzymol., 80, 303–311(1981)).

After human prothrombin, as a substrate, is reacted with a sample, the amount of the resulting thrombin can be measured by using a synthetic substrate. The prothrombin activator of the present invention can be easily discriminated from the known one by the measurement in the presence of $Ca^{2+}$ ions, for example in the presence of 3 mM $Ca^{2+}$ ions, or in the absence of $Ca^{2+}$ ions.

The N-terminal amino acid sequence of a peptide was analyzed by a sequencer in a manner known per se in the art.

The activator of the present invention can be used as a reagent for measuring the amount of prothrombin in the sample of a living body, because it does not react with PIVKA-II.

For the above object, the sample of the living body is reacted with an activator of the present invention and then the amount of the resulting thrombin is measured. For the measurement of the thrombin amount, the method in a manner known per se in the art, for example, the use of a synthetic substrate or measurement of the time for blood coagulation can be employed.

The reagent for measuring prothrombin in the sample of the living body, which pertains to the present invention, can be prepared by the method known to date. For example, the reagent can be prepared by mixing adsorption plasma deficient in a coagulation factor to be measured, an optimum amount of calcium and a prothrombin activator of the present invention derived from the snake venom.

The prothrombin activator of the present invention can be prepared by separation and purification of the naturally-existing prothrombin activator derived from the snake venom. It is also possible to obtain the activator by chemical synthesis in a known manner or by a gene recombination technique. The present invention also embraces the amino acid sequences substituted, depleted, inserted or modified in one or more than one portion thereof or even an portion of the amino acid sequence insofar as it manifests activity.

The present invention will hereinafter be described in detail by Examples but it should however be borne in mind the present invention is not limited by them.

EXAMPLES

Example 1
Process for the Purification of the Invention Activator

Figure 1:
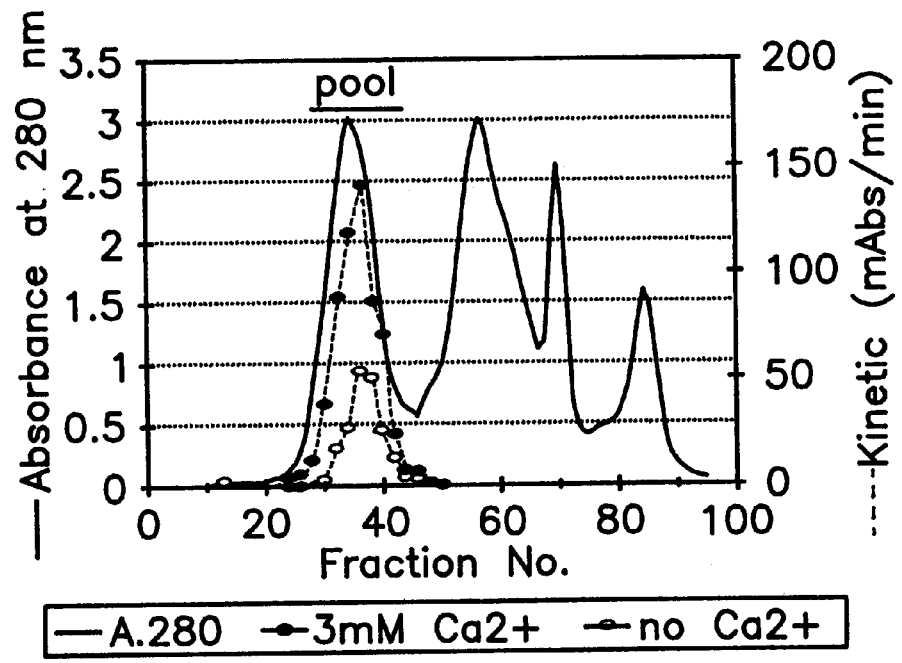
FIG. 1 illustrates an elution pattern of 100 mg of the venom of *Echis carinatus leucogaster* as a result of the chromatography on a column of Superdex 200 pg.

First, 100 mg of a venom of *Echis carinatus leucogaster* were fractionated on the column (size: 1.6×60 cm) of Superdex 200 pg. In FIG. 1, an elution pattern of one-ml aliquots collected using a 50 mM Tris-HCl buffer (pH 8.0) at a flow rate of 1 ml/min is shown. The prothrombin activating activity of each fraction was measured. As a result, it has been confirmed that the activation amount is larger under the conditions (indicated by a closed circle) where 3 mM $Ca^{2+}$ ions are present than under the conditions (indicated by an open circle) where 3 mM $Ca^{2+}$ ions are absent. Activity shown under the conditions where $Ca^{2+}$ ions is absent is brought by ecarin, which is a conventionally known prothrombin activator. Existence of another novel activator has therefore been found according to the measurement under the presence of $Ca^{2+}$ ions.

Figure 2:
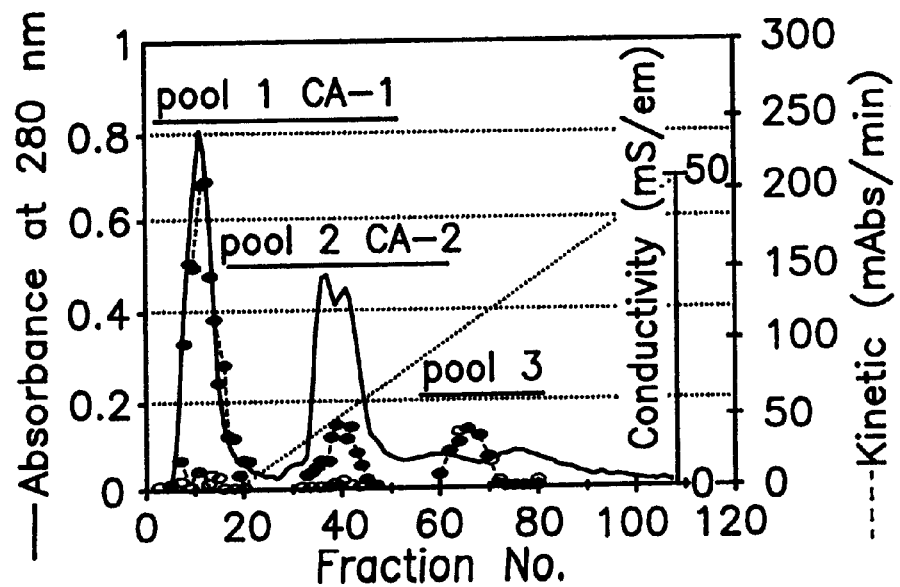
FIG. 2 illustrates an elution pattern of the active fraction obtained in FIG. 1 as a result of chromatography on a column of Blue-Sepharose CL 6B, in which pool 1, pool 2 and pool 3 correspond to CA-1, CA-2 and a conventional prothrombin activator, respectively.

The active fractions (Fr. No. 30-42) were then pooled and subjected to a column of BLUE SEPHAROSE CL 6B (size: 1.0×20 cm). After elution with the initial 50 mM tris-HCl buffer (pH 8.0), elution was effected by a concentration gradient (100 ml-100 ml) of NaCl in the same buffer (0 M to 1 M; 2 ml each). As shown in the elution pattern and activity distribution in FIG. 2, three peaks of activity were recognized: pool 3 (Fr. No. 60-70) was ecarin known to date, while pool 1 (Fr. No. 8-17) and pool 2 (Fr. No. 35-44) manifested strong activity in the presence of $Ca^{2+}$ ions, which were designated carinactivase-1 (CA-1) and carinactivase-2 (CA-2), respectively.

Figure 3:
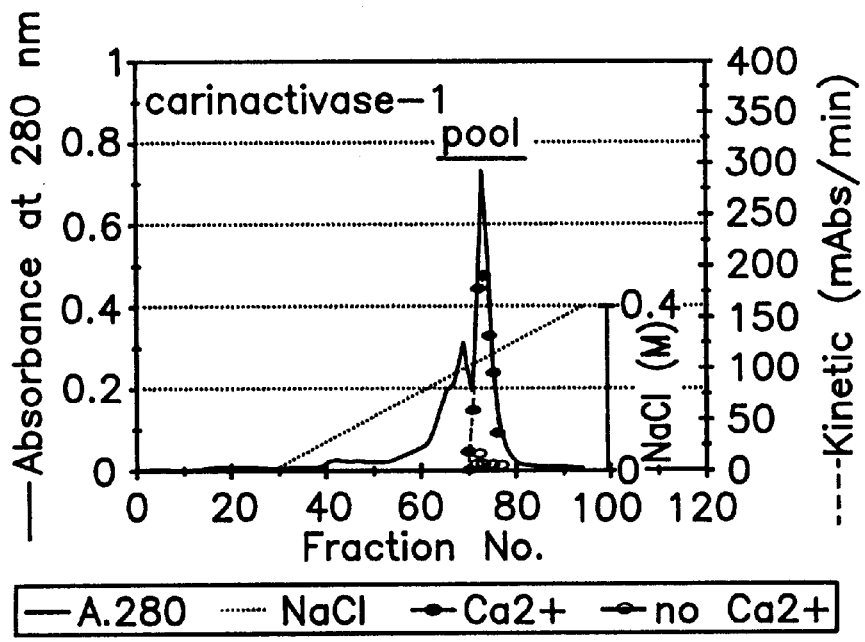
FIG. 3 illustrates an elution pattern of the CA-1 and CA-2 fractions obtained in FIG. 2 as a result of the chromatography on a column of Q Sepharose H.P.
Figure 3:
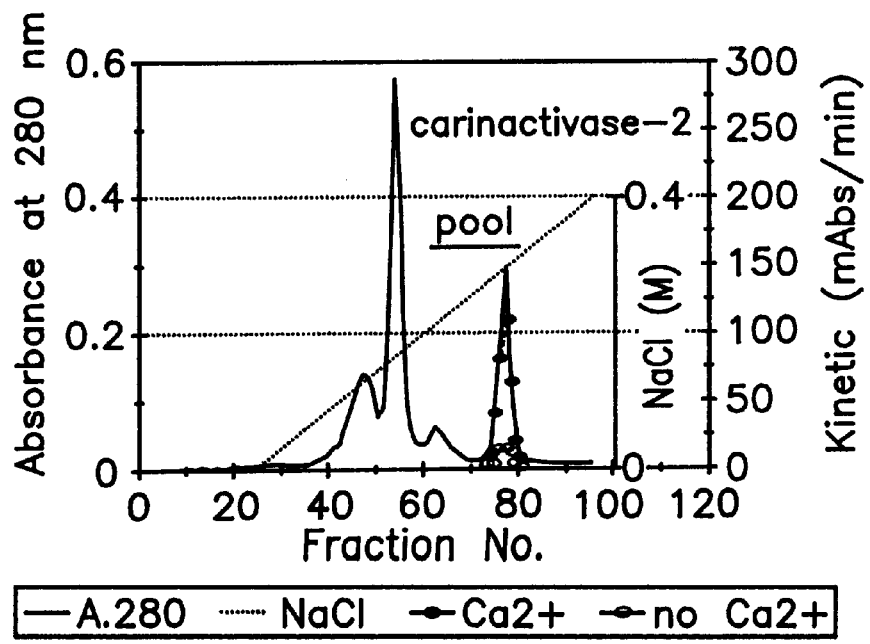

The pool 1 and pool 2 so obtained were then purified using a column of Q Sepharose H.P. (size: 1.6×20 cm). The sample was charged in the column thoroughly buffered with a 50 mM Tris-HCl buffer (pH 8.0), followed by elution with a concentration gradient of NaCl up to 0.4 M. The eluate was fractionated 2 ml by 2 ml at a flow rate of 1.0 ml/min. As a result, it has been presumed that as shown in FIG. 3, each of CA-1 and CA-2 is a pure product judging from that the activity peak coincides with the elution peak and the peak is sharp.

Example 2
Assay of Prothrombin Activation

The prothrombin activating capacity of the prothrombin activator of the present invention was assayed by the following method.

The human prothrombin (10 μM/TBS, containing 5 mM $CaCl_2$) and a sample to be tested were reacted at 37° C. for 30 minutes. To the reaction mixture, 100 mM EDTA was added in an amount one tenth of the reaction mixture, whereby the reaction was terminated. The amount of thrombin generated was quantified by measuring the activity of the resulting thrombin with VPR-pNA (Boc-Val-Pro-Arg-p-nitroanilide) as a substrate. Described specifically, 10 μl of 5 mM VPR-pNA were added to 90 μl of the reaction mixture (diluted as needed) whose reaction had already been terminated and they were reacted at 37° C. The initial velocity of p-nitroaniline liberation was measured by monitoring at 405 nm through a kinetic plate reader (manufactured by Seikagaku Kogyo Co., Ltd.).

Example 3
Determination of the Molecular Weight and N-terminal Amino Acid Sequences of CA-1 and CA-2

Figure 4:
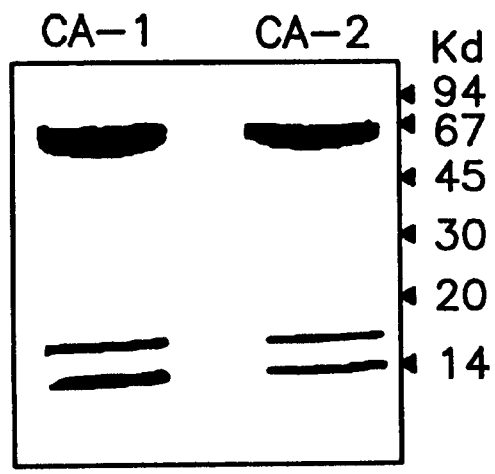
FIG. 4 illustrates SDS-PAGE of the reductants of the purified target products of CA-1 and CA-2. The heavy chain, light chain 1 and light chain 2 are shown in the order of the molecular weight.

Under reducing conditions, CA-1 and CA-2 obtained in Example 1 were analyzed by SDS-PAGE. As shown in FIG. 4, it has been confirmed that each of them is composed of three peptides, that is, a component (heavy chain) having a molecular weight of about 62,000 or about 60,000 and components (light chains) having molecular weight of about 17,000 and about 14,000 and that the light chains are linked through a disulfide bond. It has been presumed that the bond between the heavy chain and the light chains are a non-covalent bond. As a result of analysis of the N-terminal amino acid sequence of each component of CA-1 by the peptide sequencer, it has been found that the heavy chain has a sequence described in SEQ ID NOS: 1, 2 or 5 and the light chain has a sequence described in SEQ ID NOS: 3, 4, 6 or 7.

Example 4
$Ca^{2+}$ Ions Requiring Property of CA-1 and CA-2

The $Ca^{2+}$ ions requiring property of the purified target products of CA-1 and CA-2 in the manifestation of activity was confirmed. The results are shown in FIG. 5.

Figure 5:
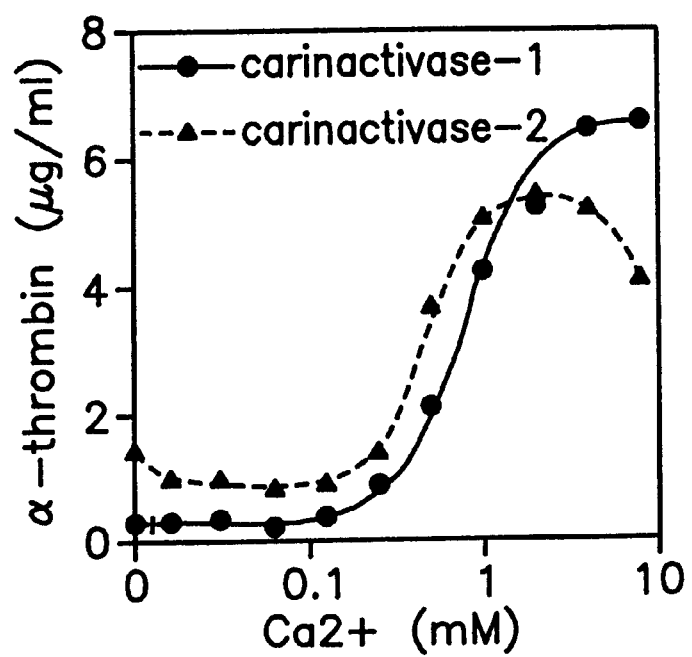
FIG. 5 illustrates prothrombin activating action of CA-1 and CA-2 on the calcium ion concentration.

As shown in FIG. 5, it has been confirmed that they manifest their activity only when $Ca^{2+}$ ions are present. In addition, they feature that they react with normal prothrombin but do not react with PIVKA-II.

Example 5
Measurement of Blood Clotting Capacity

The blood clotting capacity of each of CA-1 and ecarin was studied.

A portion (50 $\mu$l) of the plasma to be tested was mixed with 50 $\mu$l of prothrombin-deficient plasma (prepared by Geroge King Inc.) and they were incubated at 37° C. for two minutes. The clotting reaction was initiated by the addition of a portion of the mixture of activator/$Ca^{2+}$ (containing (i) 1 nM factor Xa plus 1 mg/ml of phospholipids [phosphatidylcholine/phosphatidylserine; 3:1, w/w], or (ii) 100 nM CA-1 dissolved in TBS containing 15 mM $CaCl_2$ or (iii) 100 nM ecarin dissolved in the same TBS), which had been equilibrated at 37° C. The time required for clot formation was measured in Amelung Caogulometer KC4A. The amount of prothrombin in the sample was determined by reference to a standard curve that had been prepared with normal plasma; the logarithm of the clotting time was plotted against the logarithm of the amount of prothrombin. The concentrations of activators were adjusted to give a clotting time of 10 to 15 seconds with normal plasma.

As a result, it has been found that ecarin reacts with not only normal prothrombin but also endogenous blood clotting inhibitor (PIVKA), while CA-1 reacts with normal prothrombin similar to Factor Xa but shows no reaction to PIVKA.

I claim:

1. An isolated, calcium-requiring type, prothrombin activating enzyme derived from snake venom, which comprises: three polypeptide chains, composed of:
   one heavy chain having a molecular weight of about 62,000 as analyzed by SDS-PAGE, and an N-terminal amino acid sequence according to SEQ.ID.No: 1, and
   two light chains having molecular weights of about 17,000 and about 14,000, respectively as analyzed by SDS-PAGE, and N-terminal amino acid sequences according to SEQ.ID.No: 3 and SEQ.ID.No: 4, respectively.

2. An isolated, calcium-requiring type, prothrombin activating enzyme derived from snake venom, which comprises: three polypeptide chains, composed of:
   one heavy chain having a molecular weight of about 60,000 as analyzed by SDS-PAGE, and an N-terminal amino acid sequence according to SEQ.ID.No: 2, and two light chains having molecular weights of about 17,000 and about 14,000, respectively as analyzed by SDS-PAGE, and N-terminal amino acid sequences according to SEQ.ID.No: 3 and SEQ.ID.No: 4, respectively.

3. The isolated, calcium-requiring type, prothrombin activating enzyme according to claims 1 or 2, which is a metalloprotease.

4. The isolated, calcium-requiring type, prothrombin activating enzyme according to claims 1 or 2, wherein the snake venom is that of *Echis carinatus*.

5. The isolated, calcium-requiring type, prothrombin activating enzyme derived from snake venom according to claims 1 or 2, which is obtained by purifying the snake venom by gel filtration chromatography, affinity chromatography and then chromatography on a strong basic resin.

6. The isolated, calcium-requiring type, prothrombin activating enzyme according to claim 5, which is a metalloprotease.

7. The isolated, calcium-requiring type, prothrombin activating enzyme according to claim 5, wherein the snake venom is that of *Echis carinatus*.

8. The isolated, calcium-requiring type, prothrombin activating enzyme according to claim 6, wherein the snake venom is that of *Echis carinatus*.

9. A reagent for measuring prothrombin in a biosample, which comprises at least one isolated, calcium-requiring type, prothrombin activating enzyme according to claims 1 or 2.

10. The reagent according to claim 9, wherein said at least one isolated, calcium-requiring type, prothrombin activating enzyme is a metalloprotease.

11. A process for the separation and purification of an isolated, calcium-requiring type prothrombin activating enzyme derived from snake venom according to claims 1 or 2, which comprises the following steps:

(a) subjecting a sample of snake venom to a conventional separating column to obtain separate fractions;

(b) determining the prothrombin activating activity of each fraction obtained in step (a);

(c) subjecting one or more fractions determined to have prothrombin activating activity in step (b) to elution on a column of BLUE SEPHAROSE® to obtain separate fractions;

(d) determining which fractions obtained in step (c) which exhibit stronger prothrombin activating activity in the presence of $Ca^{2+}$ ions than in the absence of $Ca^{2+}$ ions;

(e) subjecting one or more of the fractions determined to have stronger prothrombin activating activity in step (d) to purification on a conventional purification column to obtain one or more isolated calcium-requiring type prothrombin activators.

* * * * *